United States Patent [19]

Cullen

[11] Patent Number: 4,992,367
[45] Date of Patent: Feb. 12, 1991

[54] ENHANCED EXPRESSION OF HUMAN INTERLEUKIN-2 IN MAMMALIAN CELLS

[75] Inventor: Bryan R. Cullen, West Caldwell, N.J.

[73] Assignee: Hoffmann-La Roche Inc., Nutley, N.J.

[21] Appl. No.: 862,082

[22] Filed: May 12, 1986

[51] Int. Cl.$^5$ .................. C07K 13/00; C07H 15/12; C12P 21/06; C12P 19/34; C12N 15/00; C12N 5/00

[52] U.S. Cl. .................. 435/69.52; 435/69.1; 435/91; 435/172.3; 435/240.2; 435/320.1; 530/350; 536/27; 935/9; 935/32; 935/39; 935/47; 935/58; 935/62; 935/70; 935/81

[58] Field of Search .................. 435/68, 70, 172.3, 91, 435/235, 320, 240.2, 172.1, 69.52; 530/351; 536/27

[56] References Cited

U.S. PATENT DOCUMENTS

| | | | |
|---|---|---|---|
| 4,304,863 | 12/1981 | Collins et al. | 435/172 |
| 4,405,712 | 9/1983 | Vande Woude | 435/5 |
| 4,738,927 | 4/1988 | Taniguchi et al. | 435/68 |

OTHER PUBLICATIONS

Law, Y. F. et al, Mol. Cell Biol., vol. 4, pp. 1469–1475 (1984).
Kaufman, R. et al, Mol. Cell Biol., vol. 5, pp. 1750–1759 (1985).
Gordon, J. W. et al, Gene, vol. 33, pp. 121–136 (1985).
Edlund et al, Science, vol. 230, pp. 912–916 (1985).
Walker et al, Chemical Abstracts, vol. 102, p. 176, Abstract #107329r (1985).
Neilsen et al, Chem. Abstracts, vol. 99, pp. 213–214. Abst. No. 188840v (1983).
Kozak, Nucl. Acids Res. 12: 3873–3893 (1984).
Butnick et al, Mol. Cell Bio. 5: 3009–3016 (1985).
Devos, et al., Nuc. Acids Res., 11:4307–4323 (1983).
Raghow, TIBS, 12:358–360 (1987).
Rosenberg et al., N. Engl. J. Med., 316:889–897 (1987).
Barr et al., International Patent Application No. WO 85/02200.
Eick et al., EMBO J. 4:3717 (1985).
Gorman et al., Proc. Natl. Acad. Sci. U.S.A. 79:6777 (1982).
Johansen et al., Proc. Natl. Acad. Sci. U.S.A. 81:7698 (1984).
Katz et al., Mol. Cell. Biol. 6:372 (1986).
Kozak, M., Cell 44:283 (1986).
Rabbitts et al., EMBO J. 4:3727 (1985).
Rosenberg et al., Science 223:1412 (1984).
Simcox et al., Mol. Cell. Biol. 5:3397 (1985).
Souza et al., European Patent Application No. 0 136 489.
Subramani et al., Mol. Cell. Biol. 2:854 (1981).
Treisman, R., Cell 42:889 (1985).
Urlaub et al., Proc. Natl. Acad. Sci. U.S.A. 77:4216 (1980).

Primary Examiner—Robin L. Teskin
Assistant Examiner—Joan Ellis
Attorney, Agent, or Firm—George M. Gould; Bernard S. Leon; William H. Epstein

[57] ABSTRACT

Methods and compositions are provided for the high level expression of human interleukin-2 in mammalian cells. This high level expression is produced by the substitution of the normal human 5' noncoding sequences and the AUG initiation codon of the interleukin-2 gene by heterologous corresponding sequences. The expression product is a glycosylated polypeptide which is similar to the natural product and which can be purified to a high degree of purity for use as a therapeutic agent.

11 Claims, 4 Drawing Sheets pBC12/RSV/IL-2/dhFr

∿ = Vector pXF3 DNA

FIGURE 2

INSULIN                  BamHI
AAC ATG GCC CTG TGG ATC CGC
    Met Ala Leu Trp Ile Arg

INTERLEUKIN-2
        RsaI
ACA ATG TAC AGG
    Met Tyr Arg pBCI2/RSV/IL-2          Site of Ligation
AAC ATG GCC CTG TGG ATC GAC AGG
    Met Ala Leu Trp Ile Asp Arg

FIGURE 4 pBC40

5' -GGTGACCAAGCTGATCCCCCCCCCCCCCCCCCACTACTCACAGTAA- 3' pBC40 T      HindIII

5' -GGTGACCAAGCTTACTCACAGTAA-   3'

ENHANCED EXPRESSION OF HUMAN INTERLEUKIN-2 IN MAMMALIAN CELLS

TABLE OF CONTENTS

1. Technical Filed
2. Background of the Invention
   2.1. Recombinant DNA Technology
   2.2. Interleukin-2 Production
3. Summary of the Invention
4. Brief Description of the Figures
5. Description of the Invention
   5.1 Preparation of a Gene for Human Interleukin-2
   5.2. Substitution of 5' Noncoding Sequences and Cloning of the Interleukin-2 Gene
   5.3. Selection of Host Cells Harboring the Interleukin-2 Gene
   5.4. Isolation of Human Interleukin-2
6. Example
   6.1. General Procedures for Recombinant Vector Preparation
      6.1.1. DNA Preparation
      6.1.2. Conditions for Enzymatic Reactions
      6.1.3. Culture Media
      6.1.4. Transformation and Transfection
      6.1.5. Cell Cultures
      6.1.6. Primer-Directed Mutagenesis
      6.1.7. Colony Hybridization
   6.2. Construction of the Interleukin-2 Expression Vector pBC12/RSV/IL-2/dhFR
      6.2.1. Preparation of the Cloning Vector
      6.2.2. Interleukin-2 Gene Fragment Preparation
      6.2.3. Insertion of Dihydrofolate Reductase Gene Sequences
      6.2.4. High Level Expression of Human Interleukin-2
   6.3. Proof of Increased Interleukin-2 Production Due to 5' Noncoding Sequence Modification
      6.3.1. Construction of Plasmid pBC40αT
      6.3.2. Functional Comparison of Vectors pBC12/RSV/IL-2, pBC40 and pBC40ΔT

1. TECHNICAL FIELD

This invention relates to compositions for the expression of heterologous genes in mammalian cells. Such compositions comprise expression vectors and the human interleukin-2 gene, which is under the control of the long terminal repeat (LTR) promoter of Rous sarcoma virus.

The present invention further relates to methods for the modification of such expression vectors to increase expression of the interleukin-2 gene in Chinese hamster ovary cells in which the 5'non-coding region and some coding region base pairs of the gene are replaced by corresponding rat insulin gene sequence.

2. BACKGROUND OF THE INVENTION

2.1. Recombinant DNA Technology

The development of recombinant DNA procedures, which are often referred to as gene-splicing or genetic engineering, has made possible the production of a wide variety of biological products. In current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites.

Once cuts have been made by a restriction enzyme in a plasmid and in a segment of foreign DNA that is to be inserted, the two DNA molecules may be covalently linked by an enzyme known as a ligase. General methods for the preparation of such recombinant DNA molecules have been described by Cohen et al. [U.S. Pat. No. 4,237,224], Collins et al. [U.S. Pat. No. 4,304,863] and Maniatis et al. [Molecular Cloning: A Laboratory Manual, 1982, Cold Spring Harbor Laboratory]. Because they illustrate much of the state of the art, these references are hereby incorporated by reference.

Recombinant DNA molecules can be used to produce the product coded for by the inserted gene sequence only if a number of conditions are met. Foremost is the requirement that the recombinant molecule be compatible with, and thus capable of autonomous replication in, the host cell. Much recent work has utilized the bacterium *Escherichia coli* (*E. coli*) as a host organism because it is compatible with a wide range of recombinant plasmids. Depending upon the vector/host cell system used, the recombinant DNA molecule is introduced into the host by transformation, transduction or transfection.

The mere insertion of a recombinant vector into a host cell will not in itself assure that significant amounts of the desired gene product will be produced. For this to occur, the foreign gene sequence must be fused in proper relationship to a signal region in the vector for DNA transcription called a promoter Alternatively, the foreign DNA may carry with it its own promoter, as long as it is recognized by the host. Whatever its origin, the promoter is a DNA sequence that is "upstream" of the foreign gene that is to be expressed which directs the binding of RNA polymerase and therefore "promotes" the transcription of DNA to messenger RNA (mRNA).

Given strong promotion that can provide large quantities of mRNA, the ultimate production of the desired gene product will depend upon the effectiveness of translation from mRNA to protein. This, in turn, is dependent upon the efficiency of ribosomal binding to the mRNA and upon the stability of the mRNA within the host cell. In eukaryotic cells, the factors governing translational efficiency are poorly understood but appear to include a favorable nucleic acid sequence surrounding an AUG codon which initiates translation [Kozak, Cell 44:283 (1986)]. Factors affecting the stability of the mRNA, which are poorly understood in both prokaryotic and eukaryotic cells, are also critical to the amount of protein production that can be obtained.

Most of the work in the recombinant DNA field to the present has focused on the use of bacterial expression systems such as *E. coli*. Yet, the use of bacterial cells has a number of undesirable aspects. For example most proteins and polypeptides produced in *E. coli* accumulate in the periplasmic space. Recovery of these gene products thus requires disruption of the cells, a process which is inefficient and which leads to a serious purification problem, as the desired product must be purified from the numerous other *E. coli* cellular constituents. Also, bacteria cannot carry out glycosylation which is needed to complete the synthesis of many interesting gene products or form the specific disulfide bonds which are essential for the proper conformation and biological activity of many eukaryotic proteins.

To overcome these deficiencies in bacterial expression systems, the attention of genetic engineers is increasingly turning to the use of eukaryotic host cells for recombinant DNA. Cells such as yeast and mammalian cells can secrete desired gene products into the culture medium and can carry out essential glycosylation processes as well. Yet, the use of mammalian cells for recombinant DNA cloning and expression also poses a host of technical obstacles that must be overcome. For example, the endogenous plasmids that have proven to be so useful in bacteria are not replicated by higher eukaryotic cells. As a result, other approaches must be taken.

One approach has been to use the lower eukaryotic yeast, *Saccharomyces cerevisiae*, which can be grown and manipulated with the same ease as *E. coli*. Yeast cloning systems are available, and through the use of such systems the efficient expression in yeast of a human interferon gene has been achieved [Hitzeman et al., Nature (London) 293:717 (1981)]. Interferon genes do not contain introns, however, and it has been found that yeast cells do not correctly transcribe at least one heterologous mammalian gene that does contain introns, the rabbit β-globin gene (Beggs et al., Nature (London) 283:835 (1980)].

In another approach, foreign genes have been inserted into mammalian cells by means of direct uptake. This has been accomplished, for example, by calcium phosphate co-precipitation of cloned genes, by which procedure about 1–2% of the cells can generally be induced to take up the DNA. Such a low level of uptake, however, produces only a very low level of expression of the desired gene product. Where mammalian cells can be found which lack the thymidine kinase gene (tk− cells), better results can be obtained by co-transformation. Tk− cells, which cannot grow in selective HAT (hypoxanthine-aminopterin-thymidine) medium, can regain this lost enzymatic activity by taking up exogenous DNA (such as herpes simplex viral DNA) containing the tk gene through calcium phosphate co-precipitation. Other DNA covalently ligated to the tk DNA or merely mixed with it will also be taken up by the cells and will often be co-expressed [see Scangos et al., Gene 14:1 (1981)].

In a third approach, viral genomes have been used as vectors for the introduction of other genes into mammalian cells, and systems based upon Simian virus 40, papillomavirus, and adenovirus genomes have been described [see P.W.J. Rigby, Expression of Cloned Genes in Eukaryotic Cells Using Vector Systems Derived from Viral Replicans, in Genetic Engineering, Vol. 3, R. Williamson, ed., Academic Press, New York, pp. 83–141 (1982) for a review]. These systems, however, suffer from the drawback of limited host cell range. Moreover, viral replication in these systems leads to host cell death. The use of retroviral DNA control elements avoids many of the disadvantages of these viral vector systems.

Gorman et al. [Proc. Natl. Acad. Sci. U.S.A. 79:6777 (1982)] have shown, for example, that the Rous sarcoma virus long terminal repeat (LTR) is a strong promoter that can be introduced into a variety of cells, including CV-1 monkey kidney cells, chicken embryo fibroblasts, Chinese hamster ovary cells, HeLa cells and mouse NIH/3T3 cells by DNA-mediated transfection.

Evidence for the regulation of gene expression by 5′ and 3′ noncoding sequences has come from the study of oncogenes and the mRNAs of higher eukaryotic cells in which the results of the elimination or modification of these sequences on gene expression have been observed. For example, Treisman [Cell 42:889 (1985)] has studied the accumulation of c-fos RNA following serum stimulation of mouse fibroblasts into which a cloned human c-fos gene (the cellular homolog of the oncogene carried by the FBJ murine osteosarcoma virus, designated c-fos$^H$) had been transfected. Ordinarily, serum stimulation of such cells causes a strong but transient burst of c-fos mRNA which reaches a maximum by 10 to 15 minutes and decreases rapidly thereafter, reaching prestimulation levels within 1 to 2 hours due to rapid degradation of the mRNA.

When the c-fos$^H$ 5′ flanking sequences are fused to heterologous genes in the absence of the normal c-fos$^H$ 3′ flanking sequences, however, the resulting genes are still inducible by serum factors but the mRNA thereby produced persists for up to 4 hours following serum stimulation. Experiments which hybrid transcription units show that only genes containing the 3′ end of the c-fos$^H$ gene and the 3′ noncoding regions show the typical rapid decrease in mRNA levels following stimulation. It may thus be that the c-fos 3′ sequences act to destabilize fusion gene RNA. and their elimination or modification may have a positive effect upon gene expression.

Further evidence for a regulatory role by 3′ noncoding sequences has come from studies by Simcox et al. [Mol. Cell. Biol. 5:3397 (1985) on the *Drosophila melanogaster* heat shock protein system. When shifted from growth at ambient temperature to 37° C., *Drosophila melanogaster* rapidly produces a number of "heat shock" proteins, among which is a major protein called hsp 70, through a process in which new mRNAs are produced and rapidly transcribed. Following a return to normal growth temperatures, transcription of the hsp 70 gene is rapidly repressed and the levels of the corresponding mRNA rapidly decline, thereby quickly terminating further hsp 70 protein production. Simcox et al. found, however, that the rapid repression of hsp 70 protein synthesis after release from heat shock is delayed when 3′ sequences have been deleted, suggesting that the 3′ sequences normally act to destabilize the hsp 70 mRNA after the temperature downshift.

Evidence pointing to an mRNA regulatory role has also been obtained for 5′ noncoding sequences. Butnick et al. [Mol. Cell. Biol. 5:3009 (1985)] have shown that a 5′ noncoding sequence containing about 550 bases (designated exon 1) of the human c-myc gene (the cellular homolog of the avian myelocytomatosis virus oncogene) affects the expression of plasmids bearing that gene in CV1 monkey kidney cells transformed with an origin-defective Simian virus 40 (designated COS cells). Transcripts from plasmids in which the 5′ noncoding sequences of the c-myc had been deleted were found to be present at a higher steady-state level than were transcripts from plasmids bearing the intact gene, suggesting that the 5′ noncoding sequences in some way act to destabilize the corresponding mRNA.

In another study, Rabbitts et al. [EMBO J. 4:3727 (1985)] have shown that the truncation of exon 1 from the c-myc gene causes an increase in the stability of c-myc mRNA in COLO 320 cells. Similarly, Eick et al. [EMBO J. 4:3717 (1985)] have demonstrated that mRNAs produced in Burkitt's lymphoma cells by c-myc genes in which there has been a translocation in exon 1 are much more stable than the normal mRNAs.

The above references all suggest that 5' and 3' noncoding regions of a variety of genes may in some way produce instability in the corresponding mRNAs transcribed from these genes. Deletion or alteration of these noncoding regions in these cases produced increased mRNA stability and, hence, an increased overall level of gene expression. Yet the effect of modification or deletion of such noncoding sequences on gene expression cannot be predicted with assurance.

For example, Johansen et al. [Proc. Natl. Acad. Sci. U.S.A. 81:7698 (1984) have varied the length of the 5' noncoding leader region in a recombinant vector system containing gene control elements fused to the *Escherichia coli* galactokinase (galk) gene. The variation in length of the noncoding region had no effect on galk expression. Similarly, Katz et al. [Mol. Cell. Biol. 6:372 (1986)] have introduced both deletions and substitutions of other sequences into the 5' untranslated leader of avian retroviral mRNAs. Generally, these deletions and substitutions caused a substantial decrease in the expression of the env gene. These decreases in expression, however, were not due to reductions in mRNA levels. It appears instead that the changes in the noncoding segments caused a translational deficiency which led to the overall reduction in expression.

2.2. Interleukin-2 Production

Interleukin-2 (IL-2) is a soluble protein which is capable of modulating lymphocyte reactivity and promoting the long-term in vitro culture of antigen-specific effector T-lymphocytes In the past, IL-2 has been produced primarily from mammalian cells that are capable of synthesizing the protein, after such cells have been stimulated with a mitogen. For example, Morgan et al. [Science 193:1007 (1976)] and Ruscetti et al. [J. Immunol. 119:131 (1977)] have recovered IL-2 from pooled normal human lymphocytes that had been stimulated with phytohemagglutinin, while Gillis et al. [Nature 268:154 (1977)] used normal DBA/2 mouse spleen cells stimulated with concanavalin A as a source of the protein. More recently, Stern [U.S. Pat. No. 4,490,289] has described the use of induced human malignant cells as a source of IL-2.

Efforts have also been made to produce IL-2 through the use of recombinant DNA methodology. For example, Taniguchi et al. [Nature 302:305 (1983)] have described the sequence analysis, cloning and expression of a complementary DNA (cDNA) coding for human IL-2 prepared from messenger RNA from the Jurkat leukemia cell line. The expression of IL-2 was carried out by Taniguchi et al. in cultured monkey COS cells although the authors stated that work on the expression of IL-2 rDNA in *E. coli* was in progress, and that from the *E. coli* system it would soon be possible to produce IL-2 in large quantities.

Rosenberg et al. [Science 223:1412 (1984)] have also expressed IL-2 in *E. coli*, using a gene isolated from the Jurkat cell line. More recently, Souza et al. [European Patent Application No. 0 136 489] have described the cloning and expression in microorganisms of chemically synthesized DNA sequences comprising structural genes coding for a polypeptide having the amino acid sequence and properties of IL-2. Souza et al. also disclose the use of synthetic genes to produce IL-2 polypeptide analogs which differ in amino acid sequence from the natural polypeptide. In the examples provided in the Souza et al. Patent application *E. coli* is the host organism.

Barr et al. [International Patent Application No. 85/02200] have recently described the cloning and expression of a chemically synthesized human IL-2 gene in yeast.

3. SUMMARY OF THE INVENTION

Methods and compositions are provided for the cloning and expression of human interleukin-2 (IL-2) in mammalian cells. Because the IL-2 is produced in mammalian cells, it is glycosylated and has disulfide bonds like the natural product.

Surprisingly high levels of expression of the human IL-2 are obtained through the use of novel cloning and expression vectors in which natural 5' noncoding sequences and the AUG initiation sequence of the IL-2 gene have been replaced by corresponding noncoding sequences from the rat insulin gene. During the construction of the vectors of the invention, minor modifications are also made in the nucleotide sequences coding for the N-terminus of the IL-2 signal polypeptide. Such modifications do not affect the IL-2 polypeptide secreted from the producing cells since the signal polypeptide is cleaved during the process of maturation.

Methods are also provided for the purification of the human IL-2 to a degree which renders the product suitable for use as a therapeutic agent.

4. BRIEF DESCRIPTION OF THE FIGURES

The present invention may be more readily understood by reference to the following figures (not drawn to scale), wherein FIG. 1 is a schematic representation of plasmid PBC12MI, the starting vector for the construction of the IL-2 expression vector;

FIG. 2 shows the structure of the novel signal peptide N-terminus in plasmid pBC12/RSV/IL-2 and the insulin and IL-2 sequences used to construct it. Specific restriction and ligation sites are underlined;

FIG. 4 shows the identity of nucleotide sequences removed from plasmid PBC40 by oligonucleotide mutagenesis. The underlined segments delineate the 24-mer primer used to carry out the deletion, which creates a novel HindIII site.

5. DESCRIPTION OF THE INVENTION

Figure 1:
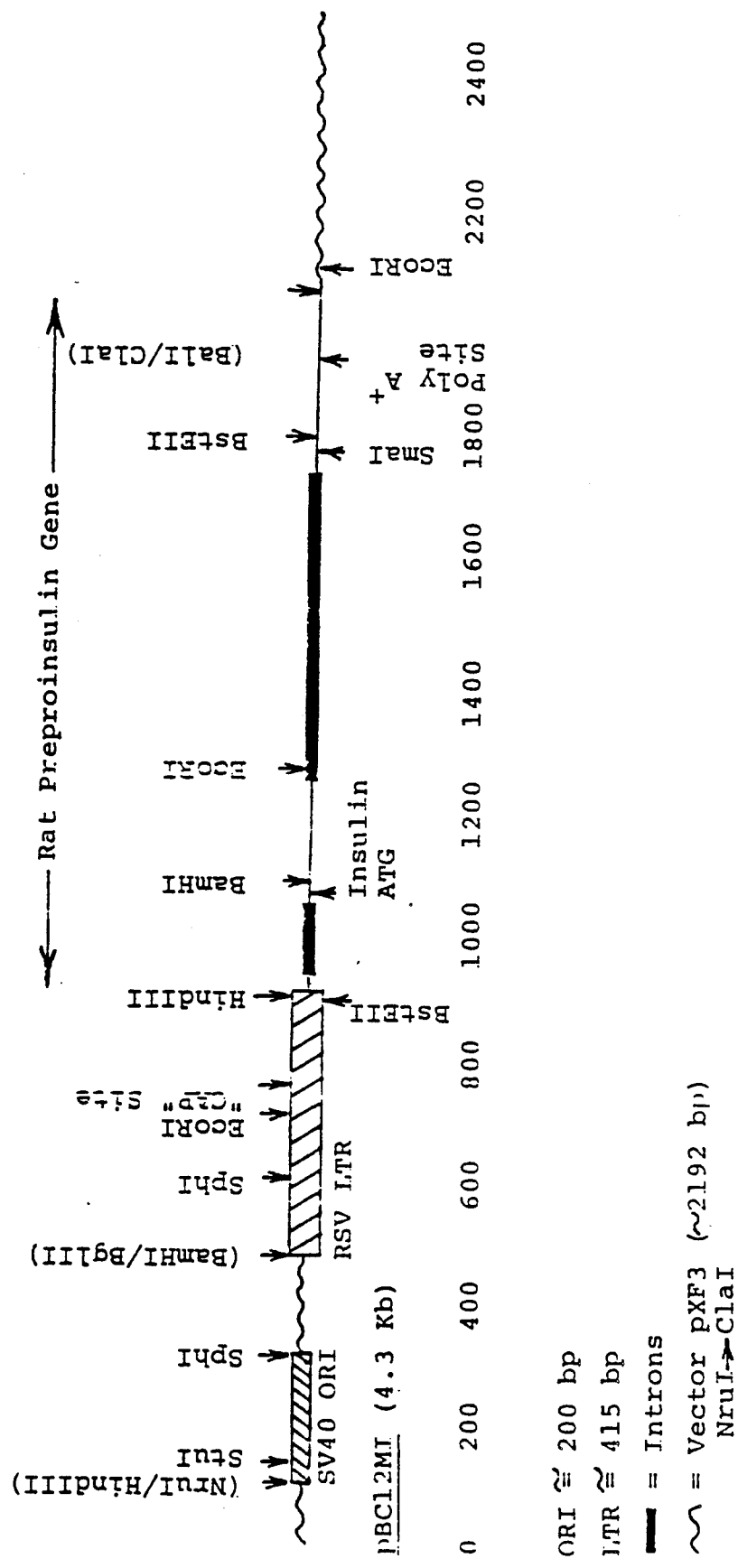

It is the surprising discovery of the present invention that the level of expression of a foreign gene in mammalian cells can be markedly increased if the normal 5' noncoding sequences of the gene are replaced in the expression vector (as used herein, the words "vector" and "plasmid" are used interchangeably) by a heterologous 5' noncoding region and initiator AUG. In the preferred embodiment of the invention, the 5' noncoding region and initiator AUG of the rat insulin gene were substituted for those of the human IL-2 gene, with the result that about a 10- to 50-fold increase in the expression of human IL-2 was obtained (see Section 6.3.2. below).

This invention therefore relates to the use of gene splicing methodology to produce human IL-2 in substantial quantities in mammalian cells. The invention further relates to the purification of the human IL-2 thus produced to a level of purity that will permit use of the IL-2 as a therapeutic agent.

The methods of the invention entail a number of steps which, in logical sequence, include (1) preparation of the gene encoding human IL-2 and a signal peptide sequence, (2) deletion of the 5' noncoding regions from the IL-2 gene, (3) replacement of the deleted regions by the corresponding regions and initiator AUG of the rat insulin gene in proper reading frame with the IL-2 gene coding region and cloning into a suitable expression vector, (4) transfer of the recombinant vector into a suitable mammalian host cell, (5) amplification of the IL-2 gene and selection of the modified mammalian host cells, and (6) identification and purification of the human IL-2 product.

5.1. PREPARATION OF A GENE FOR HUMAN INTERLEUKIN-2

As used herein the term "interleukin-2" or "IL-2" denotes a glycosylated protein that is produced by a mammalian cell that has been transformed or transfected with a human interleukin-2 gene or a modification of the human interleukin-2 gene that encodes a protein having: (a) an amino acid sequence that is at least substantially identical to the amino acid sequence of native human interleukin-2 and (b) has biological activity that is common to native human interleukin-2. Substantial identity of amino acid sequences means the sequences are identical or differ by one or more amino acid alterations (deletions, additions or substitutions) that do not cause an adverse functional dissimilarity between the synthetic protein and native human interleukin-2.

Examples of such proteins are the IL-2s described in European Patent applications No. 82307036.2 and 83101035.0, and U.S. Pat. Nos. 4,518,584 and 4,569,790. These IL-2s are produced in bacterial systems which express mature IL-2. It would be within the skill of the art to produce similar variations wherein the IL-2 genes also code for a signal peptide sequence as in the present invention.

A gene for human interleukin-2 which also encodes a signal peptide sequence can be prepared by any of the ways commonly used in the art. For example, a human cell line capable of synthesizing IL-2 can be stimulated to make IL-2 mRNA which can serve as a template to make IL-2 cDNA. Rosenberg et al. [Science 223:1412 (1984)] have used a human leukemic T-cell line and normal human peripheral blood lymphocytes, and Taniguchi et al. [Nature 302:305 (1983)] have used a human leukemic T-cell line to make such cDNA.

Alternatively since Taniguchi et al. have disclosed the nucleotide sequence, the human IL-2 gene could be chemically synthesized using the phosphotriester or another method, preferably in a solid-phase system. One such chemical synthesis has been described by Souza et al. [European Patent Application No. 0 136 489]. By synthesizing relatively small oligonucleotides and then ligating them together, Barr et al. [International Patent Application No. WO 85/02200] have also prepared the human IL-2 gene. By still another method, genomic DNA could be isolated from a human cell capable of making IL-2 and the gene could be identified by standard hybridization methods using a labeled DNA probe based upon the published sequence of the IL-2 gene.

In an illustrative embodiment of the invention, plasmid PIL-2-2b, which contains a cDNA copy of the entire 459 bp coding region of human IL-2 flanked by 31 bp of 5' nontranslated sequence and 309 bp of 3' non-translated sequence, was used as the source of the gene. The cloning of this IL-2 cDNA copy into plasmid PIL-2-2b has been described by Smith et al. [Proc. Natl. Acad. Sci. U.S.A. 82:8405 (1985)]. Due to the method used to clone the IL-2 cDNA, the nucleotide sequences are flanked by homopolymeric G-C tails, which in turn are flanked by BamHI sites.

5 2. Substitution of 5' Noncoding Sequences and Cloning of the Interleukin-2 Gene Replacement of 5' noncoding sequences and insertion of the IL-2 gene into an appropriate expression vector are easily accomplished when the requisite DNA sequences and cloning vector have been cut with the same restriction enzyme or enzymes, since complementary DNA termini are thereby produced. If this cannot be accomplished, it may be necessary to modify the cut ends that are produced by digesting back single-stranded DNA to produce blunt ends, or by achieving the same result by filling in the single-stranded termini with an appropriate DNA polymerase such as the Klenow fragment of DNA polymerase I. In this way, blunt-end ligation with an enzyme such as T4 DNA ligase may be carried out.

For insertion of the IL-2 gene into a vector, any site desired could also be produced by ligating nucleotide sequences (linkers) onto the DNA termini Such linkers may comprise specific oligonucleotide sequences that encode restriction site recognition sequences. The cleaved vector and the modified IL-2 gene may also be modified by homopolymeric tailing, as described by Morrow [Methods in Enzymology 68:3 (1979)].

In the practice of the invention, all of the 5' noncoding sequences of the human IL-2 gene must be replaced with the corresponding sequences of the rat insulin gene. It may also be possible to delete some of the adjacent coding sequences of the gene, since these sequences encode the signal polypeptide which is ultimately cleaved during maturation within the host cell into which the IL-2 gene will be inserted and expressed. Of course, deletion of too extensive a region of the coding sequences could abolish signal polypeptide function, thereby interfering with proper secretion of the product IL-2 from the cells.

In the exemplary embodiment of the invention, a eucaryotic expression vector designated PBC12MI was used both as the expression vehicle and as the source of rat preproinsulin-II gene sequences. Substitution of the 5' noncoding regions thus occurred after an IL-2 gene in which the natural 5' noncoding region had been deleted was inserted into vector pBC12MI in juxtaposition with rat insulin 5' noncoding sequences.

Vector pBC12MI is similar to the eucaryotic expression vector pBC12BI, which has been described in detail by Butnick et al. [Mol. Cell. Biol. 5:3009 (1985)]. This vector is based upon the pBR322-derived plasmid vector pXF$_3$ [Hanahan, J. Mol. Biol. 166:577 (1983)] and also contains an SV40 ori region and the efficient long terminal repeat (LTR) promoter of Rous Sarcoma Virus [Cullen et al., Nature 307:241 (1984)] and a genomic copy of the rat insulin-II gene [Lomedico et al., Cell 18:545 (1979)]. Vector pBC12MI used in the present constructions is identical to pBC12BI except that the LTR fragment contained therein extends an additional 70 bp in the 3' direction (see FIG. 1). This difference has no effect on the level of expression of genes encoded by the vector.

Of course an IL-2 gene in which the 5' noncoding regions and the AUG initiation codon had already been replaced with those from a rat insulin gene could instead be produced first, either by restriction endonuclease cleavage followed modified IL-2 gene could be inserted into an appropriate vector.

Expression vectors suitable for use in mammalian cells which could be used in this invention include but are not limited to pBC12MI, pBC12BI, PSV2dhFr, P91023(B), PcDV1 and PRSVcat. These vectors can be introduced into suitable mammalian host cells by transformation, transduction or transfection.

5.3. Selection of Host Cells Harboring the Interleukin-2 Gene

Many of the cloning vehicles that may be used in this invention contain genes (selectable genes) which encode one or more marker activities that may be used to select for desired transformants such as ampicillin resistance in pBC12BI and pBC12MI and dihydrofolate reductase activity in PSV2-dhFr. Selection of host cells into which such vectors have been inserted is greatly simplified when the host cells otherwise lack the activity contributed by the vector. In such cases the cells can be grown under restrictive conditions in which only the transformants harboring the plasmid activity can multiply.

In the preferred embodiment of the invention, the IL-2-producing plasmid provided dihydrofolate reductase activity to Chinese hamster ovary cells which otherwise lacked such activity (CHO-dhFr⁻cells). Transformants were easily selected from untransformed cells in medium lacking hypoxanthine and thymidine.

The presence of an activity in a plasmid that is lacking in host cells can provide yet another advantage in addition to a means of transformant selection. Under restrictive growth conditions transformed cells which conrain high levels of the dhFr gene will grow more rapidly than cells expressing low levels of dhFr. Such conditions will therefore select for cells which have increased or "amplified" the number of copies of the dhFr gene they express. Where a gene that is to be expressed is also present in the plasmid near the selectable gene, expression of the desired gene will be co-amplified with the additional copies of the selectable gene produced. In the present invention, culturing transformants in the presence of increasing levels of amethopterin, an inhibitor of de novo purine synthesis, caused the production of increasing levels of both dihydrofolate reductase and IL-2. This process is called "co-amplification".

Any similar selectable gene system could be used in the present invention, although not all systems will produce amplification. Another system which could be used but which will not produce amplification, for example, is based upon the E. coli gpt gene, which encodes xanthine-guanine phosphoribosyl transferase. Mulligan et al. [Proc. Natl. Acad. Sci. U.S.A. 78:2072 (1981)] have selected monkey and mouse cells transfected with plasmids bearing the gpt gene by growing the cells in the presence of mycophenolic acid (an inhibitor of de novo guanylic acid synthesis), adenine and xanthine. Selection in this system is further enhanced by the addition of aminopterin (an analog of amethopterin) to the selection medium.

Still another system involves the gene for a bacterial aminoglycoside 3' phosphotransferase, the product of which renders bacteria resistant to neomycin and kanamycin. Colbere-Garapin et al. [J. Mol. Biol. 150:1 (1981)] have selected mammalian cells transfected with plasmids bearing the pnosphotransferase gene under the control of the HSV tk gene promoter by growing the cells in the presence of G-418, a 2-deoxystreptamine antibiotic which inhibits eucaryotic protein synthesis. Berg [Science 213:296 (1981)] has achieved the same result with a series of pSV vectors in which the phosphotransferase gene was under SV40 control.

5 4. Isolation of Human Interleukin-2

The human IL-2 secreted by the producing cells can be identified in the culture medium by any of the methods known in the art. For example, a bioassay based upon the use of cells that are dependent upon IL-2 for proliferation can be used, or a radioimmunoassay or enzyme-linked immunosorbent assay could be carried out using antibodies against IL-2. Polyacrylamide gel electrophoresis followed by Western blot or similar analysis could also be used. Alternatively, analysis by high performance liquid chromatography (HPLC) could be carried out as described by Stern [U.S. Pat. No. 4,490,289].

The human Il-2 of the invention can be concentrated by precipitation with salts such as sodium or ammonium sulfate, by ultrafiltration or by the use of other methods well known to those skilled in the art. Further purification can be accomplished by conventional protein purification techniques including but not limited to gel filtration, ion-exchange chromatography, preparative disc-gel or curtain electrophoresis, isoelectric focusing, low temperature organic solvent fractionation, HPLC or countercurrent distribution. Methods described by Stern, supra, are preferably used.

6. EXAMPLE

The following is a non-limiting example which illustrates the methods by which the cloning and expression of human IL-2 in mammalian cells was carried out and provides proof of the substantial enhancement in gene expression that is attributable to substitution of the normal 5' noncoding regions of the human IL-2 gene by those of the rat insulin gene.

6.1. General Procedures for Recombinant Vector Preparation

6.1.1. DNA Preparation

Small scale isolation of plasmid DNA from saturated overnight cultures was carried out according to the procedure of Birnboim et al. [Nucleic Acids Research 7:1513 (1979)]. This procedure allows the isolation of a small quantity of DNA from a bacterial culture for analytical lo purposes. Unless otherwise indicated larger quantities of plasmid DNA were prepared as described by Clewell et al. [J. Bacteriol. 110:1135 (1972)]. Specific restriction enzyme fragments derived by the cleavage of plasmid DNA were isolated by preparative electrophoresis in 1% low melting 15 aqarose (Seaplaque, FMC Inc., Rockland, Me.). Nine×5½ cm gels were run at 50 mA for 1 hour in Tris-Acetate buffer [Maniatis et al., Molecular Cloning: A Laboratory Manual, 1982, Cold Spring Harbor Laboratory, p. 454] and then stained with 1 μg/ml ethidium bromide to visualize the DNA. Appropriate gel sections were excised and melted at 65° C. for 10 minutes and then diluted with 5 ml of a low salt buffer containing 0.2 M NaCl. 20 mM Tris-HCl (pH 7.4) and 1 mM EDTA. The DNA was then concentrated using an ElutiP-D column (Schleicher and Schuell Inc., Keen, N.H.) following the manufacturer's instructions and precipitated at −20° C. with ethanol in the presence of 10 μg of tRNA carrier (yeast, Bethesda Research Laboratories, Bethesda, Md.).

6.1.2. Conditions for Enzymatic Reactions

The restriction enzymes, DNA polymerase I (Klenow fragment) and T4 DNA ligase were products of New England Biolabs, Mass., and the methods and conditions for the use of these enzymes were essentially those of the manufacturer.

For the restriction endonucleases, a unit of activity is defined as the amount of enzyme needed to produce a complete digest of 1.0 $\mu$g DNA in 60 minutes in a total reaction volume of 0.05 ml, with digestion carried out at 37° C. The buffer used for all of these enzymes (hereinafter referred to as restriction enzyme buffer) consisted of 100 mM NaCl, 10 mM Tris-HCl (pH 7.5), 5 mM $MgCl_2$ and 1 mM 2-mercaptoethanol.

T4 DNA ligation was carried out for 16 hours at 4° C. in a buffer (hereinafter called ligation buffer) containing 60 mM Tris-HCl (pH 7.5), 10 mM $MgCl_2$, 10 mM dithiothreitol and 0.1 mM ATP. A unit of T4 DNA ligase activity is defined as the amount required to give 50% ligation of HindIII fragments of lambda DNA in 30 minutes at 16° C. in 20 $\mu$l of incubation mixture and a 5' DNA termini concentration of 0.12 $\mu$M (300 $\mu$g/ml).

Klenow blunt-ending of single-stranded DNA ends was carried out in restriction enzyme buffer which had been adjusted to contain 1 mM dGTP, dATP dCTP and TTP. A unit of activity is defined as the amount converting 10 nmoles of deoxyribonucleotides to an acid insoluble form in 30 minutes at 37° C.

6.1.3. Culture Media

Iscove's Modified Eagle's Medium (IMEM) was obtained from Grand Island Biological Co., Grand Island, N.Y.

Luria Broth (LB) contained 5 g Bacto-yeast extract, 10 g Bacto-tryptone and 10 g NaCl per liter, adjusted to pH 7.5.

The antibiotic ampicillin was added to a final concentration of 50 $\mu$g/ml where indicated.

6.1.4 Transformation and Transfection

*Escherichia coli* strains were transformed by the method of Peacock et al. [Biochim. Biophys. Acta 655:243 (1981)], essentially as follows. The cells were harvested from LB medium and prepared for transformation by the method of Norgard et al. [J. Biol. Chem. 255:7665 (1980)] except that the $CaCl_2$ buffer instead contained 70 mM $MnCl_2$, 40 mM NaOAc and 30 mM $CaCl_2$, pH 5.6.

A 100 $\mu$l sample of cells suspended in the $CaCl_2$ buffer was combined with 50 $\mu$l of plasmid sample containing between 50 and 1,000 ng of DNA. The mixture Was kept on ice for 1 hour and then heated at 37° C. for 2 minutes. The cells were plated on 4° C. LB agar plates with ampicillin and incubated for 16 hours at 37° C. to select for transformants.

Chinese hamster ovary cells were transfected by the method of Graham et al. [Virology 52:456 (1973)] as follows. Five-tenths ml of a mixture containing 8 g/l NaCl. 0.37 g/l KCl, 0.125 g/l $Na_2HPO_4.2H_2O$ 1 g/l dextrose, 3 g/l Tris and 125 mM $CaCl_2$, with 10 $\mu$g total DNA were added to $5 \times 10^5$ cells in a 6 cm culture dish containing 4 ml of IMEM supplemented with $10^{-4}$ M hypoxanthine and $1.0^{-5}$ M thymidine (HT). The DNA in that mixture consisted of 5 $\mu$g of calf thymus high molecular weight carrier DNA, and 5 $\mu$g of pBC12/RSV/IL-2/dhFr DNA which had been cleaved at the unique PvuI site.

The culture was incubated overnight at 37° C. in a humidified 5% $CO_2$ incubator, after which the medium was removed and replaced with 5 ml of fresh IMEM supplemented with $10^{-4}$ M hypoxanthine and $10^{-5}$ M thymidine (HT). After one day of further incubation the cells were detached from the dish using a trypsin-EDTA solution (GIBCO) and plated into two 10 cm dishes in 20 ml of IMEM with 10% dialyzed fetal calf serum (FCS) but without HT. Transfectant colonies were isolated using a standard cloning cylinder technique after 10 days of further incubation at 37° C.

African green monkey kidney cells (COS) were transfected using methods described by Butnick et al. [Mol. Cell. Biol. 5:3009 (1985)]. Ten cm tissue culture dishes were seeded with $3 \times 10^6$ COS cells in 10 ml of IMEM supplemented with 10% FCS and 50 $\mu$g/ml qentamycin and incubated overnight in a 37° C., 5% $CO_2$ humidified incubator. The cells were then washed once with 37° C. phosphate buffered saline (PBS), and 2 ml of 37° C. PBS containing 500 $\mu$g/ml of DEAE-dextran (Pharmacia) and the DNA to be transfected were added to the cells. The COS cells were then incubated and gently shaken at 5-minute intervals over a 30-minute period.

After this incubation, 20 ml of IMEM containing 10% FCS, 50 $\mu$g/ml gentamycin and 80 $\mu$M chloroquin were added to each dish. After 2½ hours of further incubation, the medium was replaced with fresh IMEM medium with 10% FCS and 50 $\mu$g/ml gentamycin. Incubation was continued at 37° C. for 72 hours, and the cells and media were then analyzed as described below.

6.1.5 Cell Cultures

Two *Escherichia coli* strains were used in the work described herein. *E. coli* strain GM119, which has been described by Marinus et al. [J. Bacteriol. 114:1143 (1973)], is available from the American Type Culture Collection under accession No. ATCC 53339. *E. coli* strain MC1061 is also available from the American Type Culture Collection (ATCC) under accession No. ATCC 53338. This strain has been described by Casadaban et al. [J. Mol. Biol. 138:179 (1980)].

Three mammalian cell lines were used. One cell line was a Chinese hamster ovary line (CHO/dhFr−) which lacks dihydrofolate reductase which was originally isolated by Urlaub et al. [Proc. Natl. Acad. Sci. U.S.A. 77:4216 (1980)]. Cultures of this cell line have been deposited with the American Type Culture Collection and assigned accession No. CRL 9096. An African green monkey kidney cell line (COS) which has been transformed by an origin minus SV40 viral genome [Gluzman, Cell 23:175 (1981)] is available from the ATCC under accession No. CRL 1651. A murine IL-2 dependent cell line (CTLL) which has been described by Robb [Methods in Enzymology 116:493 (1985)] is available from the ATCC under accession No. TIB 214.

6.1.6. Primer-Directed Mutagenesis

Primer-directed site specific mutagenesis was performed according to the methods described by Morinaga et al. [Biotechnology 2:636 (1984)]. The synthetic oligonucleotide used to carry out the mutagenesis procedure was prepared by the phosphoramidite solid support method of Matreucci et al., J. Am. Chem Soc. 103:3185 (1981).

6.1.7. Colony Hybridization

Colony hybridization was performed using a method described by Maniatis et al. [Molecular Cloning: A Laboratory Manual, 1982, Cold Spring Harbor Laboratory, pp. 312–315]. The same oligonucleotide used for primer-directed mutagenesis was used as a probe for the hybridizations after 5' end labeling with $\gamma$-$^{32}$P-ATP using polynucleotide kinase according to the procedure of Maniatis et al., supra, p. 396. The labeling of larger DNA probes to locate the IL-2 and dhFr genes was carried out using a nick translation kit (Amersham) according to the manufacturer's instructions.

6.2. Construction of the Interleukin-2 Expression Vector pBC12/RSV/IL-2/dhFr The preparation of the final expression vector of the invention was carried out in stages, entailing in succession (1) preparation of a vector into which a modified human IL-2 gene could be inserted, (2) modification of the IL-2 gene to delete most of the 3' noncoding region, all of the 5' noncoding sequences and coding sequences corresponding to two amino acids from the N-terminus of the IL-2 signal polypeptide, and (3) insertion of the modified gene into the prepared vector.

6.2.1. Preparation of the Cloning Vector

One $\mu$g of plasmid pBC12MI DNA (see FIG. 1) was treated with 20 units of BamHI in 100 $\mu$l of restriction enzyme buffer for 1 hour at 37° C. This plasmid has been deposited with the American Type Culture Collection and assigned accession No. ATCC 67109. The reaction mixture was then blunt-ended by Klenow fragment treatment with 4 units of enzyme for 2 hours at 15° C., after which the reaction was stopped by heating to 65° C. for 5 minutes. Two $\mu$l of the mixture were then diluted 1:10 with ligation buffer and the mixture was cooled on ice. One unit of T4 DNA ligase was added, and the reaction mixture was incubated for 16 hours at 4° C.

The ligation reaction mixture was then used directly to transform E. coli strain GM119, and transformants were selected in LB agar with ampicillin. The DNA from ampicillin resistant colonies thus obtained was screened by restriction endonuclease cleavage with BamHI or ClaI followed by analysis of the DNA fragments produced by electrophoresis in a 1% agarose gel containing 10 $\mu$g/ml ethidium bromide. One plasmid which had lost the BamHI site but acquired a ClaI site in its place was thus identified and designated plasmid pBC12CI.

Plasmid pBC12CI was then prepared in larger quantity by the detergent lysis procedure of Clewell et al. [J. Bacteriol. 110:1135 (1972)]. Final preparation of the cloning vector was carried out by cleaving 1 $\mu$g of pBC12CI with 20 units of ClaI and blunt-ending the digestion product with Klenow fragment DNA Polymerase I.

6.2.2. Interleukin-2 Gene Fragment Preparation

As noted above plasmid pIL-2-2b containing a cDNA copy of the entire 459 bp coding region of human IL-2 flanked by 31 bp of 5' non-translated sequence and 309 bp of 3 non-translated sequence [Taniguchi et al., Nature 302:305 (1983)], was used as a source of the IL-2 gene. Ten $\mu$g of PIL-2-2b were cleaved with 20 units each of RsaI and BamHI in 100 $\mu$l of restriction enzyme buffer for 1 hour at 37° C. RsaI cleaves the IL-2 cDNA insert at a single site 1 bp 3' to the IL-2 initiation codon. The reaction mixture was then treated with Klenow fragment DNA polymerase I and subjected to preparative electrophoresis in a 1% low melting agarose gel. The desired 760 bp RsaI/BamHI IL-2 cDNA fragment was identified and extracted from the gel as described in Section 6.1.1.

One-hundred ng of the prepared vector pBC12CI were mixed with 100 ng of the RsaI/BamHI IL-2 fragment in 30 $\mu$l of ligation buffer containing 2 units of T4 DNA ligase and incubated overnight at 4° C. The ligated DNA was then used to transform E. coli strain MC1061, and transformants were selected on LB agarose plates with ampicillin.

Two-hundred ng of the isolated IL-2 fragment were used to generate a $^{32}$P labeled nick-translated probe using the Amersham nick translation kit according to the manufacturer's instructions. Colonies from the plates were lifted onto nitrocellulose filters (Schleicher and Schuell Inc.) and then screened for the presence of the IL-2 insert using the labeled probe and following the procedures of Maniatis et al. [Molecular Cloning: A Laboratory Manual, 1982, Cold Spring Harbor Laboratory]. Hybridization positive colonies were picked and DNA mini-preparations were made by the Birnboim et al. procedure. These preparations were cleaved with HindIII and StuI and screened by gel electrophoresis for the presence of a characteristic 690 bp fragment which is indicative of the correct construction. This construction was designated pBC10.

A larger quantity of pBC10 DNA was prepared, and 10 $\mu$g were cleaved with 20 units of HindIII and 16 units of StuI in restriction enzyme buffer for 1 hour at 37° C. The resulting 690 bp IL-2 DNA fragment was isolated by preparative agarose gel electrophoresis as previously described.

One $\mu$g of plasmid pBC12MI DNA was cleaved with BamHI and then treated with Klenow DNA polymerase as described in Section 6.2.1. After incubation at 65° C., the DNA was cleaved with HindIII, extracted with aqueous phenol-chloroform and precipitated by the addition of a half-volume of 7.5 M ammonium acetate and 2 volumes of ethanol, followed by incubation at −70° C. The precipitated pBC12MI DNA was recovered by centrifugation, washed with ethanol and resuspended in water.

One-hundred ng of the prepared pBC12MI vector was ligated to 200 ng of the isolated IL-2 HindIII/StuI fragment in 30 $\mu$l of ligation buffer as previously described. The ligation mixture was used to transform E. coli strain MC1061, and transformants were selected on LB agarose plates with ampicillin. Individual colonies were screened as before for the presence of a 690 bp HindIII/BamHI fragment, and a construction meeting this criterion was designated pBC12/RSV/IL-2.

As thus constructed, plasmid pBC12/RSV/IL-2 contains a chimeric human IL-2 gene in which the 5' noncoding region and the initiator AUG of IL-2 as well as nearly the entire 3' noncoding region have been replaced by sequences derived from the rat insulin-II gene present in the pBC12MI vector. In part, this construction was made to produce a defined 3' noncoding region. But it is the substitution of the 5' noncoding region which, as will be shown below, produces a marked increase in the level of expression of the IL-2 gene. The resulting structure of the IL-2 signal peptide N-terminus is shown in FIG. 2.

As shown in FIG. 2, this construction results in the formation of a chimeric signal peptide in which the first two amino acids of IL-2 (Met-Tyr) are replaced by the first five amino acids of the rat insulin signal peptide (Met-Ala-Leu-Trp-Ile), and a sixth amino acid is created at the ligation junction (Asp). This change has no effect on the function of the signal peptide, which is cleaved from the IL-2 gene during maturation as usual.

6.2.3. Insertion of Dihydrofolate Reductase Gene Sequences

One µg of pBC12/RSV/IL-2 was cleaved with StuI, and the DNA was phenol/chloroform extracted, precipitated with ethanol and resuspended in water. Ten µg of PSV2dhFr DNA [Subramani et al., Mol. Cell. Biol. 1:854 (1981)] were cleaved with PvuII and BamHI. Plasmid PSV2dhFr has been deposited with the American Type Culture Collection and assigned accession No. ATCC 67110. The resulting SV40/dhFr gene fragment was isolated in a 1% preparative agarose gel, after which 100 ng of the pBC12/RSV/IL-2 vector were ligated to 400 ng of the isolated SV40/dhFr fragment in 40 µl of ligation buffer at 4° C. overnight. The ligation mixture was used to directly transform *E. coli* strain MC1061, and transformants were selected on LB agarose plates with ampicillin.

Transformed colonies were lifted onto nitrocellulose filters and screened using a $^{32}$P nick translation labeled probe prepared against the isolated SV40/dhFr gene fragment. The probe was prepared by labeling 200 ng of the isolated PvuII/BamHI SV40/dhFr fragment using the Amersham nick-translation kit as described above. Hybridization positive colonies were further screened using the Birnboim et al. procedure and gel electrophoretic analysis for the presence of two BamHI fragments.

Figure 3:
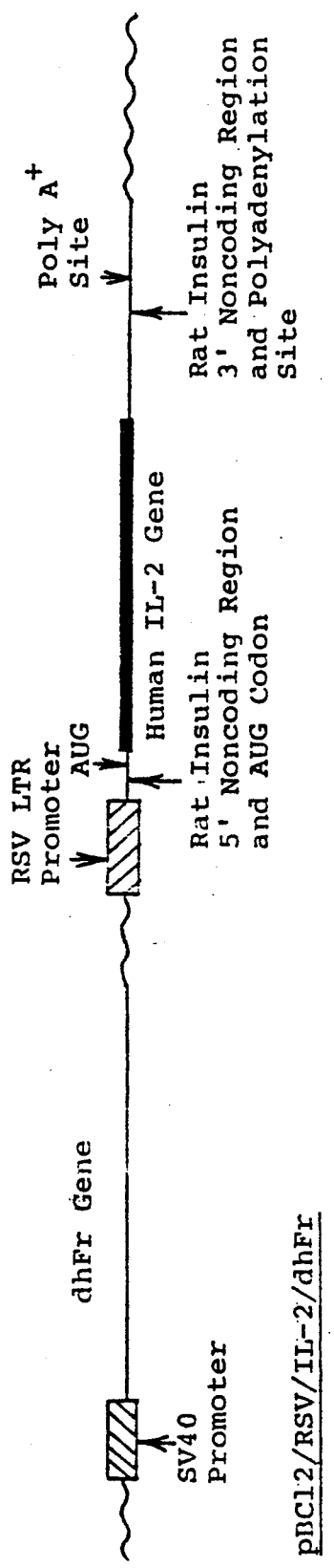
FIG. 3 is a schematic representation of the final IL-2 expression vector, PBC12/RSV/IL-2/dhFr.

The presence of the BamHI fragments confirmed the presence of the SV40/dhFr fragment and established the orientation of the fragment. The SV40/dhFr gene fragment cloned into pBC12/RSV/IL-2 contains an entire murine dhFr gene under the control of the SV40 virus early region promoter. A clone was chosen in which the IL-2 and dhFr genes in the plasmid were positioned in the same orientation, and the plasmid of this clone was designated pBC12/RSV/IL-2/dhFr (see FIG. 3).

6.2.4. High Level Expression of Human Interleukin-2

To express the IL-2 gene, one day prior to transfection $5 \times 10^5$ CHO/dhFr$^-$ cells were plated in a 6 cm tissue culture dish in 4 ml of IMEM supplemented with $10^{-4}$ M hypoxanthine and $10^{-5}$ M thymidine (HT). After incubation overnight in a 37° C. humidified 5% CO$_2$ incubator, the cells were transfected with pBC12/RSV/IL-2/dhFr and transfected colonies were isolated (see Section 6.1.4).

Cloned colonies designated d51 - d56 were thus obtained, each of which was grown in IMEM and screened against the others and against an uncloned mixed dhFr$^+$ culture (designated d5) for IL-2 production using a quantitative bioassay based on the murine IL-2 dependent cell line CTLL. This assay, which has been described by Robb [Methods in Enzymology 116:493 (1985)], entails mixing a range of two-fold dilutions of the supernatant media from the different dhFr$^+$ cell clones with the murine IL-2 dependent cell line CTLL. Because the CTLL line will only grow in the presence of IL-2, the degree of proliferation of these cells, as determined by their incorporation of $^3$H-dT, is an accurate measure of the level of IL-2 secreted by the dhFr$^+$ clones. The results of this analysis of the cloned colonies are shown in Table 1, where the data are expressed as IL-2 activity in terms of both units/ml of medium and units/10$^6$ cells. A unit of IL-2 activity is defined as the reciprocal of the dilution corresponding to the half-maximal proliferation response adjusted by the response of the IL-2 standard available from the Biological Response Modifiers Program of the National Cancer Institute, Frederick, Md. [Thurman, Lymphokine Res. 31:227 (1984)] as described by Robb, supra.

TABLE 1

| | Comparison of IL-2 Production by Isolated Clones | | |
|---|---|---|---|
| | Amethopterin Concentration | Interleukin-2 Activity | |
| Clone | (Molar) | (units/ml) | (units/10$^{-6}$ cells) |
| d5 | 0 | 640 | 456 |
| d51 | 0 | 1,920 | 1,370 |
| d52 | 0 | 1,920 | N.D. |
| d53 | 0 | 1,920 | 1,580 |
| d54 | 0 | 820 | N.D. |
| d55 | 0 | 550 | N.D. |
| d51 | $5 \times 10^{-6}$ | 51,200 | 60,160 |
| d51 | $2 \times 10^{-5}$ | 51,200 | 80,210 |
| d51 | $8 \times 10^{-5}$ | 76,800 | 150,400 |
| d51 | $2 \times 10^{-4}$ | 76,800 | 156,900 |
| d51 | $5 \times 10^{-4}$ | 153,600 | 401,000 |

N.D. = Not determined

In Table 1 it can be seen that clones d51 and d53 were the strongest producers of IL-2 activity. To demonstrate the selectable gene amplification effect mentioned in Section 5.3, clone d51 cells were grown for 7 to 14 day periods in increasingly higher levels of amethopterin until a line resistant to a $5 \times 10^{-4}$ M concentration of the inhibitor was obtained. As shown in Table 1, this cell line secreted high levels of human IL-2. As expected, analysis of the cells by Southern analysis [Maniatis et al., Molecular Cloning: A Laboratory Manual, 1982, Cold Spring Harbor Laboratory, pp. 382–389] showed that each contained about 100 copies of the pBC12/RSV/IL-2/dhFr Plasmid.

6.3. Proof of Increased Interleukin-2 Production Due to 5′ Noncoding Sequence Modification The homopolymeric G-C tails originally added to the IL-2 cDNA copy to facilitate cloning into plasmid PIL-2-2b (see Section 5.1) have an inhibitory effect upon the expression of the IL-2 gene. To properly compare the rates of IL-2 expression between gene sequences having the normal human 5′ noncoding regions and sequences in which these regions were replaced by those from the rat insulin gene, a plasmid was thus prepared in which the inhibitory homopolymeric tails were deleted. This plasmid was designated pBC40ΔT.

6.3.1. Construction of Plasmid pBC40ΔT

A cut vector into which the Il-2 gene could be cloned was prepared by cleaving 1 µg of pBC12MI with 20 units of BamHI and 20 units of HindIII in restriction enzyme buffer for 1 hour at 37° C. The resulting fragment was then treated with Klenow DNA polymerase, extracted with phenol/chloroform and precipitated as described above.

An IL-2 DNA fragment was prepared by cleaving 10 µg of PIL-2-2b DNA with 20 units of BamHI and 8 units of StuI and blunt-ended with Klenow DNA polymerase. An approximately 550 bp IL-2 fragment was then isolated from a 1% preparative agarose gel as described above.

One-hundred ng of the prepared vector pBC12MI were then ligated to 150 ng of the IL-2 BamHI/StuI fragment in 25 μl of ligation buffer as described previously. The ligation mixture was used directly to transform E. coli strain MC1061, and transformants were selected on LB agarose plates with ampicillin. Ampicillin-resistant colonies were lifted from the plates onto nitrocellulose filters and screened for the presence of the IL-2 insert by colony hybridization with a $^{32}P$ labeled nick-translated probe prepared against 200 ng of the purified BamHI/StuI fragment with the Amersham kit.

Hybridization positive colonies were picked and screened for the presence of an approximately 560 bp BstEII/BamHI fragment by the Birnboim et al. method, and a construction designated pBC40 was identified. Plasmid pBC40 is identical to pBC12/RSV/IL-2 except that it lacks the insulin 5' noncoding region and instead has the natural 31 bp human IL-2. 5' nontranslated region. The plasmid also retains the natural IL-2 initiation codon and has the 17 bp homopolymeric tail which is located in the 5' noncoding region. A larger quantity of pBC40 DNA was prepared by the method of Clewell et al. [J. Bacteriol. 110:1135 (1972)].

The homopolymeric tail segment of the IL-2 gene was deleted by the primer-directed mutagenesis method of Morinaga et al. [Biotechnology 2:636 (1984)]. To carry out this procedure, a phosphorylated 24-mer deoxyoligonucleotide primer was prepared by the phosphoramidite solid support method as described above which contained 12 deoxynucleotides complementary to the bases on each side of the homopolymeric region to be removed on one of the DNA strands. The nucleotide sequence of this 24-mer primer and that of the DNA containing the homopolymeric region to be excised are shown in FIG. 4. Regions which undergo hybridization during the process of mutagenesis are underlined. Deletion of the homopolymeric region creates a novel HindIII site in the resulting DNA.

To carry out the mutagenesis procedure, 1 μg of pBC40 DNA was linearized with PvuI, extracted with phenol/chloroform, precipitated in ethanol and taken up in 20 μl of water. Ten μg of additional pBC40 were cleaved with EcoRI, and the largest vector fragment produced, called the "gapped vector", was isolated in a 1% preparative agarose gel.

Equal 200 ng quantities of the linearized and gapped plasmids were then mixed with a 20-fold molar excess of the phosphorylated oligonucleotide in 10 μl of water, and 2 μl of 10x Klenow buffer [1 M NaCl, 65 mM Tris-HCl (pH7.4), 45 mM $MgCl_2$ and 10 mM 2-mercaptoethanol] were added. The mixture was treated for successive periods of 5, 30, 30 and 5 minutes at 100° C., room temperature, 4° C. and on ice, respectively, after which the sample was made up to a volume of 20 μl by the addition of 2 μl of 10 mM ATP, 4 μl of a mixture of 2.5 mM dCTP, dATP, dGTP and TTP, 0.5 μl of Klenow polymerase I (2.5 units of activity) and 1 μl of T4 DNA ligase (0.8 units of activity).

The mixture was incubated for 16 hours at 15° C. and then used directly to transform E. coli strain MC1061. Transformants were selected on LB agarose plates with ampicillin, and colonies from the plates were lifted onto nitrocellulose filters and screened for the presence of a sequence homologous to the 24-mer primer used in the mutagenesis procedure using the synthetic oligonucleotide labeled with $α-^{32}P$-ATP as a probe.

Positive colonies were further screened by the method of Birnboim et al. for the presence of an expected 530 bp HindIII/BamHI fragment. Because colonies obtained by this procedure are mixed (Morinaga et al., supra), a positive DNA sample was used to retransform E. coli MC1061, and resulting colonies were rescreened for the 530 bp HindIII/BamHI fragment. A positive colony thus identified, which was designated pBC40ΔT, was identical to pBC40 but for the deletion of a 22 bp segment in the untranslated leader consisting primarily of the 17 bp homopolymeric G-C sequence.

6.3.2. Functional Comparison of Vectors pBC12/RSV/IL-2, pBC40 and pBC40ΔT

The three constructions described above were compared for their ability to direct the synthesis of human IL-2 using the transfected COS cell quantitative transient expression assay of Butnick et al. [Mol. Cell. Biol. 5:3009 (1985)]. In this procedure, equimolar amounts of the DNA preparations to be compared are introduced by transfection into the African green monkey kidney cell line COS described by Gluzman [Cell 23:175 (1981)]. which is transformed by an origin minus SV40 viral genome. Deoxyribonucleic acids containing an SV40 origin of replication (such as the test plasmids) which are introduced into these cells are replicated to a high copy number and are thus efficiently expressed by the SV40 dependent DNA replication machinery present in the cells.

The levels of IL-2 produced by the transformed COS cells were determined using the quantitative CTLL cell line bioassay of Robb (see Section 6.2.4), with the results shown in Table 2 for four different experiments.

TABLE 2

| Effect of 5' Noncoding Sequences on Interleukin-2 Expression | | | | | |
|---|---|---|---|---|---|
| | Relative IL-2 Production (Units/ml) | | | | |
| Clone | 1 | 2 | 3 | 4 | Average (%) |
| pBC12/RSV/IL-2 | 1,024 | 512 | 1,536 | 6,144 | 100 |
| pBC40 | 24 | 8 | 32 | 192 | 2.8 |
| pBC40ΔT | 128 | 96 | 128 | 768 | 12.1 |

As shown in Table 2, plasmid pBC12/RSV/IL-2 directs the synthesis of considerably higher levels of IL-2 than do plasmids pBC40 and pBC40ΔT. Although the presence of a homopolymeric region in the 5' noncoding region of pBC40 makes it less effective than pBC40ΔT, the principal difference among the three plasmids lies in the fact that the bulk of the 5' untranslated sequences of pBC40 and pBC40ΔT are natural human sequences, while in plasmid pBC12/RSV/IL-2 the corresponding sequences from the rat insulin gene are present.

The substitution of the normal human 5' noncoding sequences by those of the rat gene markedly enhances IL-2 expression for reasons that are unclear. Although an understanding of the mechanism of this enhanced expression is not essential to the invention, it may be that increased mRNA stability is responsible for the effect. Conversely, it is possible that substitution of the insulin initiator AUG codon for the natural IL-2 AUG codon (FIG. 2) confers a higher translational efficiency due to the more ideal sequence adjacent to the insulin initiation codon [Kozak, Cell 44:283 (1986)].

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. A DNA sequence coding for human interleukin-2 and a human interleukin-2 signal peptide sequence, which DNA sequence comprises a gene coding for human interleukin-2 and a human interleukin-2 signal peptide sequence in which the 5' noncoding sequence of the gene has been replaced by the entire 5' noncoding sequence of the rat preproinsulin II gene.

2. A recombinant vector comprising a vector and a DNA sequence coding for human interleukin-2 and a human interleukin-2 signal peptide sequence, which DNA sequence comprises a gene coding for human interleukin-2 and a human interleukin-2 signal peptide sequence in which the 5' noncoding sequence of the gene has been replaced by the entire 5' noncoding sequence of the rat preproinsulin II gene, wherein the recombinant vector is capable of directing expression of the DNA sequence in a mammalian cell.

3. The recombinant vector according to claim 2 in which the vector comprises from 5' to 3' an SV40 ori region, a long terminal repeat promoter of Rous sarcoma virus and a rat insulin-II gene.

4. A cultured mammalian cell containing a recombinant vector comprising a vector and a DNA sequence coding for human interleukin-2 and a human interleukin-2 signal peptide sequence, which DNA sequence comprises a gene coding for human interleukin-2 and a human interleukin-2 signal peptide sequence in which the 5' noncoding sequence of the gene has been replaced by the entire 5' noncoding sequence of the rat preproinsulin II gene, wherein the mammalian cell is capable of expressing the DNA sequence.

5. The mammalian cell according to claim 4 in which the cell is a CHO/dhFr⁻ cell.

6. A process for producing human interleukin-2, comprising:
   (a) Culturing a mammalian cell containing a recombinant vector comprising a vector and a DNA sequence coding for human interleukin-2 and a human interleukin-2 signal peptide sequence, which DNA sequence comprises a gene coding for human interleukin-2 and a human interleukin-2 signal peptide sequence in which the 5' noncoding sequence of the gene has been replaced by the entire 5' noncoding sequence of a rat preproinsulin II gene, under conditions in which the DNA sequence is expressed; and
   (b) isolating human interleukin-2 from the culture.

7. The process according to claim 6 in which the recombinant vector is introduced into the mammalian cell by transfection.

8. The process according to claim 6 in which the recombinant vector contains a selectable gene and the mammalian cell is cultured in a selection medium, whereby multiple copies of the selectable gene and the DNA sequence coding for human interleukin-2 are produced by co-amplification.

9. The process according to claim 8 in which the selectable gene codes for dihydrofolate reductase, the mammalian cell otherwise lacks dihydrofolate reductase activity and the selection medium lacks hypoxanthine and thymidine and contains amethopterin.

10. The process according to claim 9 in which the mammalian cell is a CHO/dhFr⁻ cell.

11. A process for transforming mammalian cell capable of producing human interleukin-2 comprising introducing a recombinant vector into a mammalian cell, which recombinant vector comprises a vector and a DNA sequence coding for human interleukin-2 and a human interleukin-2 signal peptide sequence, which DNA sequence comprises a gene coding for human interleukin-2 and a human interleukin-2 signal peptide sequence in which the 5' noncoding sequence of the gene has been replaced by the entire 5' noncoding sequence of the rat preproinsulin II gene.

* * * * *